(12) United States Patent
Bekemeier et al.

(10) Patent No.: US 9,005,640 B2
(45) Date of Patent: *Apr. 14, 2015

(54) FABRIC AND FIBRE CONDITIONING ADDITIVES

(75) Inventors: Thomas Bekemeier, Midland, MI (US); Lorry Deklippel, Piâton (BE); Tatiana Dimitrova, Braine l'Alleud (BE); Russell Elms, Midland, MI (US); Fabrizio Galeone, Buvrinnes (BE); Bertrand Lenoble, Silly (BE); Leon Marteaux, Auderghem (BE); Josef Roidl, Saulheim (DE); Martin Severance, Midland, MI (US); Stephane Ugazio, Soignies (BE); Brett Zimmerman, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 188 days.

This patent is subject to a terminal disclaimer.

(21) Appl. No.: 13/124,325

(22) PCT Filed: Oct. 15, 2009

(86) PCT No.: PCT/US2009/060836
§ 371 (c)(1),
(2), (4) Date: Aug. 9, 2011

(87) PCT Pub. No.: WO2010/045454
PCT Pub. Date: Apr. 22, 2010

(65) Prior Publication Data
US 2011/0293677 A1   Dec. 1, 2011

Related U.S. Application Data

(60) Provisional application No. 61/140,221, filed on Dec. 23, 2008, provisional application No. 61/176,226, filed on May 7, 2009, provisional application No. 61/181,728, filed on May 28, 2009.

(30) Foreign Application Priority Data

Oct. 15, 2008   (GB) .................................. 0818864.1

(51) Int. Cl.
| | | |
|---|---|---|
| *A61K 8/02* | (2006.01) | |
| *C11D 3/00* | (2006.01) | |
| *A61K 8/11* | (2006.01) | |
| *C11D 3/16* | (2006.01) | |
| *C11D 3/37* | (2006.01) | |
| *C11D 17/00* | (2006.01) | |

(52) U.S. Cl.
CPC ............. *C11D 3/0015* (2013.01); *A61K 8/11* (2013.01); *C11D 3/162* (2013.01); *C11D 3/3742* (2013.01); *C11D 17/0039* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 5,035,832 A | 7/1991 | Takamura et al. | |
| 5,506,201 A | 4/1996 | McDermott et al. | |
| 6,013,682 A | 1/2000 | Dalle et al. | |
| 6,251,313 B1 | 6/2001 | Deubzer et al. | |
| 6,303,149 B1 | 10/2001 | Magdassi et al. | |
| 6,737,444 B1 | 5/2004 | Liu | |
| 6,767,883 B2 | 7/2004 | Barbuzzi et al. | |
| 7,056,880 B2 | 6/2006 | Wang et al. | |
| 8,071,132 B2 * | 12/2011 | Adair et al. ................. | 424/489 |
| 2004/0131570 A1 | 7/2004 | Suenaga et al. | |
| 2007/0088122 A1 | 4/2007 | Liles et al. | |
| 2008/0027172 A1 | 1/2008 | Gee et al. | |
| 2011/0158923 A1 | 6/2011 | Galeone et al. | |
| 2011/0165206 A1 | 7/2011 | Liu et al. | |
| 2011/0236498 A1 | 9/2011 | Marteaux et al. | |
| 2011/0311723 A1 | 12/2011 | Bekemeier et al. | |
| 2012/0021023 A1 | 1/2012 | Bekemeier et al. | |
| 2012/0101227 A1 | 4/2012 | Galeone et al. | |

FOREIGN PATENT DOCUMENTS

| | | |
|---|---|---|
| EP | 0590538 A1 | 4/1994 |
| EP | 0941761 A2 | 9/1999 |
| EP | 0958804 A2 | 11/1999 |
| WO | WO 02087522 A2 | 11/2002 |
| WO | WO 03066209 A1 | 8/2003 |
| WO | WO 2006063483 A1 | 6/2006 |
| WO | WO 2006072083 A1 | 7/2006 |
| WO | WO 2007049188 A1 | 5/2007 |
| WO | WO 2008002637 A2 | 1/2008 |
| WO | WO 2010045440 A1 | 4/2010 |
| WO | WO 2010045446 A2 | 4/2010 |

OTHER PUBLICATIONS

English language abstract for EP 0941761 extracted from the espacenet.com database on Oct. 11, 2011, 9 pages.
Dr. Alan Rawle, "Basic Principles of Particle Size Analysis", Malvern Instruments Limited, WR14 1XZ, UK, accessed on Oct. 11, 2011 through website: http://www.rci.rutgers.edu/~moghe/PSD%20Basics.pdf, 8 pages.
International Search Report for Application No. PCT/US2009/060817 dated Feb. 15, 2010, 3 pages.
International Search Report for Application No. PCT/US2009/060824 dated Jun. 16, 2010, 4 pages.
International Search Report for Application No. PCT/US2009/060836 dated Feb. 15, 2010 4 pages.

* cited by examiner

*Primary Examiner* — Hasan Ahmed

(74) *Attorney, Agent, or Firm* — Howard & Howard Attorneys PLLC

(57) ABSTRACT

A fabric, fiber, hair or skin conditioning additive for use in a liquid cleaning product is encapsulated within a shell comprising a silicon-containing polymer network.

17 Claims, 2 Drawing Sheets

FABRIC AND FIBRE CONDITIONING ADDITIVES

RELATED APPLICATIONS

Figure 1A:
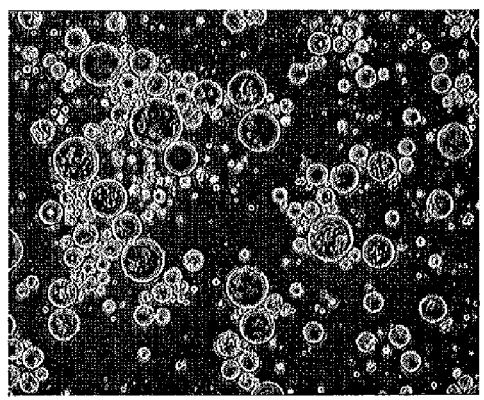
Figure 1A:
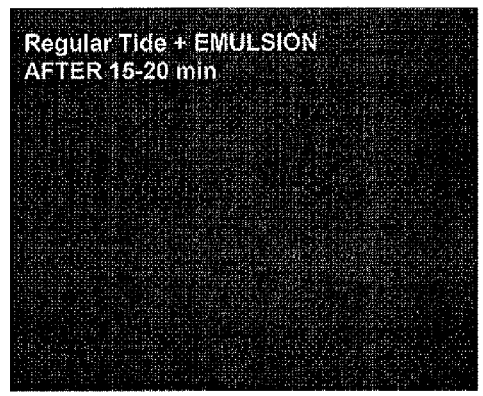
Figure 1A:
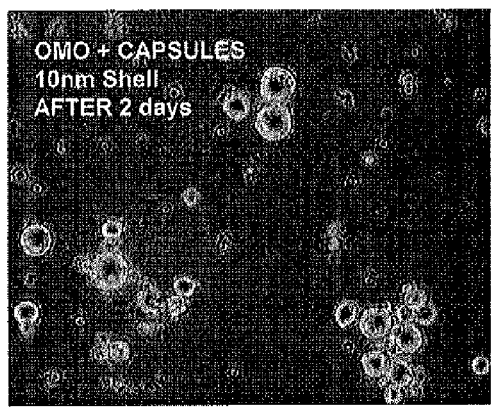
Figure 1A:
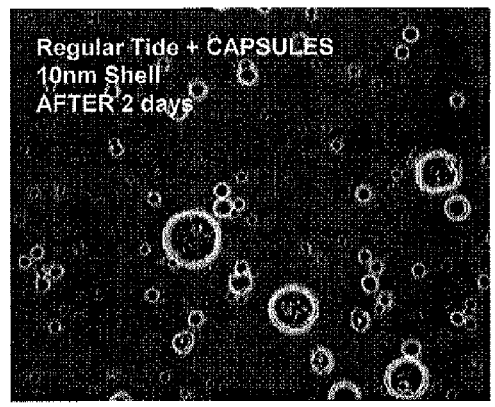

This application claims priority to and all the advantages of International Patent Application No. PCT/US2009/060836, filed on Oct. 15, 2009, which claims priority to Great Britain Patent Application No. GB0818864.1, filed on Oct. 15, 2008, U.S. Provisional Patent Application No. 61/140,221, filed on Dec. 23, 2008, U.S. Provisional Patent Application No. 61/176,226, filed on May 7, 2009, and U.S. Provisional Patent Application No. 61/181,728, filed on May 28, 2009.

This invention relates to active materials like additives for conditioning, for example for softening substrates like fabric, skin, hair and/or fibres. In particular it relates to additives intended to be added to liquid cleaning products, for example liquid laundry detergents, hair shampoos, body liquid shampoos, shower gels. The invention also relates to liquid cleaning products containing the fabric, skin, hair and/or fibre conditioning additives.

Many conditioning compositions are known for fabric and fibres, for example fabric softeners and hair conditioners. There is a demand for a conditioning composition that can be incorporated in a liquid cleaning product so that washing and conditioning can be carried out in a single process. However there is a risk that the conditioner is washed off the fabric or fibre by the cleaning product. This is especially a problem in a liquid laundry detergent, since such detergents generally use strong anionic surfactants and contain anti-deposition agents to prevent re-deposition of dirt, and are applied with a washing step followed by extensive rinsing of the fabric.

Skin and/or hair cleaning compositions (as for example shower gels and the like) comprise typically about 10-12% surface active materials as ionic and nonionic surfactants, which tend to dry/irritate the skin and impart an unpleasant feel. Lipophilic skin conditioning agents, as for example dimethiconol and vegetable oil (jojoba, aloe vera, chamomile extract etc.), which confer pleasant feel (frequently described as smooth and silky touch) and soothe irritated and problematic skin are known in the art. However, lipophilic skin conditioners are prone to solubilisation in the surfactant-rich base of typical skin/hair cleaning compositions. The solubilised species are generally washed away and do not deposit on the skin/hair.

WO-A-2007/049188 describes fabric laundering compositions containing organosilicone fabric softeners which are formulated into microemulsions for improved deposition onto fabrics.

US-A-2004-121930 describes the use of cationic celluloses to enhance deposition of water insoluble fabric care benefit agents such as dispersible polyolefins and latexes from laundry compositions during laundering.

WO-A-2006/072083 describes liquid laundry detergent compositions containing a quaternary ammonium fabric-softening agent and a silicone copolyol carboxylate which will complex with the quaternary softening agent.

U.S. Pat. No. 5,506,201 discloses a method for producing a fragrance-containing solid particle of improved substantivity for incorporation into laundry detergents which comprises of a fat component and a solid surface active agent like sorbitan ester.

U.S. Pat. No. 6,303,149 describes a process for preparing sol-gel microcapsules loaded with functional molecules by emulsifying sol-gel precursors and the functional molecules in an aqueous solution, and mixing the emulsion with an acidic, neutral or basic aqueous solution to obtain a suspension of microcapsules.

EP-A-941761 describes a process for preparing microcapsules with an organopolysiloxane shell and a core material, in which the shell is formed in situ by hydrolysis and polycondensation of an organosilane and/or a condensation product thereof having at most 4 silicon atoms. WO-A-03/066209 describes a lipophilic cosmetic, chemical, biological or pharmaceutical active material composition such as a sunscreen encapsulated within a shell of the emulsion polymerisation product of a tetraalkoxysilane. WO-A-2008/002637 discloses a process for preparing microcapsules by mixing an oil phase and an aqueous solution of a cationic surfactant to form an oil in water emulsion, and adding a water reactive silicon compound comprising tetraalkoxysilane to the emulsion so that the tetraalkoxysilane condenses and polymerises at the oil/water interface. The amount of cationic surfactant is 0.1% to 0.3% by weight based on the oil phase and the shell thickness of the microcapsules is at least 18 nm.

A fabric, skin or fibre conditioning additive according to the invention for use in a liquid cleaning product comprises an active material composition, preferably a fabric or fibre conditioner, which is encapsulated within a shell comprising a silicon-containing polymer network.

The invention also includes the use of an encapsulated polyorganosiloxane as fabric softener in a liquid laundry detergent composition.

The invention includes a process for preparing an encapsulated fiber or fabric conditioning additive comprising adding a liquid composition comprising a water reactive silicon compound (composition A) to an aqueous emulsion of a fibre or fabric conditioner (composition B), thereby condensing and polymerising the composition A at its interface with the emulsified droplets of the composition B to form microcapsules, the latter having a core of the fibre or fabric conditioner composition B surrounded by a shell comprising a silicon-based polymerized network.

The shell comprising a silicon-containing polymer network can be formed from a water reactive silicon compound comprising tetraalkoxysilane which is added to an aqueous emulsion of the active material composition. The water reactive silicon compound condenses and polymerises at the interface of the emulsified droplets of the lipophilic active material composition to form microcapsule. The microcapsules have a core of the active material composition surrounded by a shell which is a silicon-based polymerized network.

Then the encapsulated material is added to a liquid cleaning formulation, for example a heavy duty liquid detergent for fabric cleaning. Because of their size the particles get trapped into the fabric during the washing process then during the spinning process the shell of the capsules tend to burst releasing the fabric care active.

The active material than can be trapped can deliver some fabric care benefits or/and some perfume during the wash cycle.

In yet another aspect of the present invention the polymeric shell protects an encapsulated lipophilic active material from being dissolved by the liquid detergent formulation or an encapsulated silicone emulsion from coalescence.

The fabric or fibre conditioning agent is generally a lipophilic material which upon deposition on a fabric or fibres confers a benefit such as softening or shine or pleasant feel (touch). Conditioning agents within the scope of this patent are for example softening agents imparting softness to laundered fabrics and conditioning agents which facilitate the combing of hair. Without being bound to a theory, we believe that deposition of the conditioning agent on the fabric or fibres reduces of the sliding friction between fibers, whether these are the individual fibers and yarns used for the fabrication of textiles or biological fibers such as hair. This reduction in sliding friction is perceived as softness in fabrics and as a soft or silky feel in hair. Skin conditioning agents confer smooth feel to the skin and soothe the irritation caused by surfactants.

The conditioning agent can for example be an agent known as a fabric softener or an agent known as a hair conditioner. Polyorganosiloxanes are preferred conditioning agents within both these categories.

One preferred type of fabric softener is an amino-functional polyorganosiloxane. The amino-functional polyorganosiloxane can for example be a substantially linear amino-functional polydiorganosiloxane having at least one aminoalkyl group bonded to silicon. The organic groups of the polydiorganosiloxane can for example be alkyl and/or aryl groups and are usually methyl groups. One example of a preferred amino-functional polydiorganosiloxane has the formula:

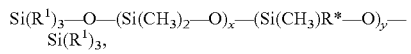

where R* is an aminoalkyl group having 1 to 18 carbon atoms and 1 to 3 nitrogen atoms, each group $R^1$ is selected from alkoxy groups having 1 to 4 carbon atoms, hydrocarbon groups having 1 to 18 carbon atoms and or aminoalkyl groups having 1 to 30 carbon atoms and 1 to 5 nitrogen atoms, and x and y are integers between 1 and 100, y being less than 0.1x. The aminoalkyl groups of the amino-functional polydiorganosiloxane are preferably of the formula:

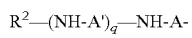

wherein A and A' are each independently a linear or branched alkylene group having 1 to 6 carbon atoms; q=0-4; $R^2$ is hydrogen or an alkyl or hydroxyalkyl group having 1 to 4 carbon atoms. Examples of preferred aminoalkyl groups include —(CH2)3NH2, —(CH2)4NH2, —$(CH_2)_3NH(CH_2)_2 NH_2$, —$CH_2CH(CH_3)CH_2NH(CH_2)_2NH_2$, —$(CH_2)_3 NHCH_2CH_2NH(CH_2)_2NH_2$, —$CH_2CH(CH_3)CH_2NH (CH_2)_3 NH_2$, —$(CH_2)_3NH(CH_2)_4NH_2$ and —$(CH_2)_3$—O—$(CH_2)_2 NH_2$.

Another preferred type of conditioning agent useful as a fabric softener is long-chain poly(organo)siloxane such as for example polydimethyl siloxane, which can be trimethyl or hydroxyl terminated. It is preferable to use DP (degree of polymerisation) of 800 and higher.

Blends of different polysiloxanes can be used, for example of a polydimethyl siloxane with an amino-functional polyorganosiloxane.

Alternative polyorganosiloxanes useful as fabric softeners include silicone polyethers having a polydiorganosiloxane moiety, for example polydimethylsiloxane, and one or more hydrophilic polyalkylene oxide, for example polyoxyethylene chains. The hydrophilic polyalkylene oxide chains can be incorporated as side chains (pendant moieties) or as block copolymer moieties with the polysiloxane moiety.

The fabric softener can alternatively be an emulsifiable organic addition polymer, for example a dispersible polyolefin such as polyethylene or polypropylene modified by the inclusion of carboxyl groups.

Preferred hair conditioners include amino-functional polyorganosiloxanes, for example substantially linear amino-functional polydiorganosiloxanes as described above. Unsubstituted polydiorganosiloxanes such as long chain polydimethylsiloxanes are also useful hair conditioners, for example the chain extended polydimethylsiloxanes produced as described in U.S. Pat. No. 6,013,682.

Preferred skin conditioners are lipophilic plant extracts (oils) and essential oils for example but not restricted to aloe vera, jojoba oil, chamomile oil; silicone based skin conditioners as dimethicone or dimethiconol, as well as synthetic oils as iso-dodecane, iso-hexadecane, paraffin, petrolatum, isononyl Isononanoate ester, octyldodecanol ester etc. These could be used alone or in combination.

The fabric or fibre conditioning agent is emulsified before being contacted with the water reactive silicon compound, so that the conditioning agent forms the disperse phase of an oil-in-water emulsion. The conditioning agent is emulsified in an aqueous medium preferably with the aid of a surfactant.

The surfactant is most preferably a cationic or amphoteric surfactant, which readily forms an emulsion of positive zeta-potential. We have found that a positive zeta-potential promotes condensation and polymerisation of the tetraalkoxysilane at the interface of the emulsified droplets of the conditioning agent, leading to more impervious microcapsules. Nonionic surfactants can be used; for example the cationic or amphoteric surfactant can be mixed with up to an equal weight of nonionic surfactant.

The concentration of surfactant in the aqueous emulsion of conditioning agent can be between 0.01 and 10% by weight, but is preferably at least 0.02% and below 2%, most preferably 0.05 to 1.5% by weight of the emulsion, particularly 0.2-1.0%. In general the use of low levels of surfactant during emulsification of the conditioning agent and reaction with the alkoxysilane leads to microcapsules which are more resistant to diffusion or leaching of the conditioning agent from the microcapsules.

Subsequent addition of surfactant to the suspension of microcapsules has less or no effect on diffusion or leaching of the conditioning agent from the microcapsules.

The weight ratio of oil phase to aqueous phase in the emulsion can generally be between 40:1 and 1:50, although the higher proportions of aqueous phase are economically disadvantageous particularly when forming an emulsion of microcapsules. Usually the weight ratio of oil phase to aqueous phase is between 2:1 and 1:10, and more preferably the oil phase (conditioning agent) forms from 10 or 20% up to 50% by weight of the emulsion. If the conditioning agent is highly viscous, a phase inversion process can be used in which the oil phase is mixed with surfactant and a small amount of water, for example 2.5 to 10% by weight based on the oil phase, forming a water-in-oil emulsion which inverts to an oil-in-water emulsion as it is sheared. Further water can then be added to dilute the emulsion to the required concentration.

Examples of cationic surfactants include quaternary ammonium hydroxides such as octyl trimethyl ammonium hydroxide, dodecyl trimethyl ammonium hydroxide, hexadecyl trimethyl ammonium hydroxide, octyl dimethyl benzyl ammonium hydroxide, decyl dimethyl benzyl ammonium hydroxide, didodecyl dimethyl ammonium hydroxide, dioctadecyl dimethyl ammonium hydroxide, cetyl trimethyl ammonium chloride, tallow trimethyl ammonium hydroxide and coco trimethyl ammonium hydroxide as well as corresponding salts of these materials, fatty amines and fatty acid amides and their derivatives, basic pyridinium compounds, quaternary ammonium bases of benzimidazolines and polypropanolpolyethanol amines.

Examples of suitable amphoteric surfactants include cocamidopropyl betaine, cocamidopropyl hydroxysulfate, cocobetaine, sodium cocoamidoacetate, cocodimethyl betaine, N-coco-3-aminobutyric acid and imidazolinium carboxyl compounds.

The above surfactants may be used individually or in combination.

Examples of non-ionic surfactants include polyoxyalkylene alkyl ethers such as polyethylene glycol long chain (12-14 C) alkyl ether, polyoxyalkylene sorbitan ethers, polyoxyalkylene alkoxylate esters, polyoxyalkylene alkylphenol ethers, ethylene glycol propylene glycol copolymers, polyvinyl alcohol and alkylpolysaccharides, for example materials of the structure $R^1$—O—$(R^2O)$m-$(G)_n$ wherein $R^1$ represents a linear or branched alkyl group, a linear or branched alkenyl group or an alkylphenyl group, $R^2$ represent an alkylene group, G represents a reduced sugar, m denotes 0 or a positive integer and n represents a positive integer as described in U.S. Pat. No. 5,035,832.

The continuous phase of the emulsion can be a mixture of water with a water-miscible organic solvent such as an alcohol or lactam provided that the continuous phase is not miscible with the conditioning agent. The particle size of the emulsion of conditioning agent can be reduced before addition of the water-reactive silicon compound, for example in an apparatus applying increased shear such as a homogeniser or microfluidiser, or a sonolator (ultrasonic mixer). The emulsion can alternatively be prepared by phase inversion.

The aqueous phase of the emulsion may contain a thickener, for example polyvinylpyrrolidone, polyvinyl alcohol, bentonite clay, a cellulose derivative, particularly a cellulose ether such as sodium carboxymethylcellulose, a lightly crosslinked acrylic polymer, modified starch, an alginate or xanthan gum, to inhibit settling of the microcapsules from the emulsion during formation or subsequently. The thickener is added to the emulsion before addition of the tetraalkoxysilane. Addition of polyvinylpyrrolidone to the emulsion before addition of the tetraalkoxysilane promotes formation of microcapsules more resistant to diffusion of the conditioner from the microcapsules for most particle sizes of the microcapsules.

The water reactive silicon compound which is added to the emulsion of conditioning agent to form the microcapsules can be any silicon compound capable of polymerizing to form a silicon-containing network polymer. Such a silicon compound generally has an average of more than 2 silicon-bonded hydrolysable groups per molecule. The hydrolysable groups are preferably alkoxy groups bonded to silicon, although alternative hydroxyl groups such as acetoxy can be used. Preferred alkoxy groups are those having 1 to 4 carbon atoms, particularly ethoxy and methoxy groups.

In one preferred embodiment the water reactive silicon compound comprises a tetraalkoxysilane. The tetraalkoxysilane can for example be tetraethoxysilane (TEOS), which can be used in monomeric form or as a liquid partial condensate.

The tetraalkoxysilane can be used in conjunction with one or more other water-reactive silicon compound having at least one, preferably at least two and most preferably three, Si—OH groups or hydrolysable groups bonded to silicon, for example an alkyltrialkoxysilane such as methyltrimethoxysilane or a liquid condensate of an alkyltrialkoxysilane, or a (substituted alkyl)trialkoxysilane. Examples of trialkoxysilanes containing substituted alkyl groups are aminoalkyltrialkoxysilanes and quaternised aminoalkyltrialkoxysilanes. One preferred type of quaternary aminosilane has the formula $R'_3$—Si-A-N(+)$R''_3$, wherein each group R' is an alkoxy group having one or two carbon atoms, each group R" is an alkyl group having 1 to 18 carbon atoms, and A is a divalent organic radical of the formula $C_nH_{2n}$ where n is an integer from 1 to 18. An example of such a quaternised aminoalkyltrialkoxysilane is dimethyl octadecyl trimethoxysilylpropyl ammonium chloride having the formula $(CH_3O)_3$ $SiCH_2CH_2CH_2N^+(CH_3)_2(CH_2)_{17}CH_3Cl^-$. The water reactive silicon compound can for example comprise 10-100% by weight tetraalkoxysilane and 0-90% trialkoxysilane, for example 10-95% tetraalkoxysilane and 5-90% trialkoxysilane, particularly a trialkoxysilane having an amino or quaternary ammonium substituted alkyl group. We have found mixtures of quaternised aminoalkyltrialkoxysilanes with tetraalkoxysilane to be particularly effective in encapsulating a polyorganosiloxane fabric softener to give controlled delivery of the softener from a liquid laundry detergent.

The tetraalkoxysilane and the trialkoxysilane, for example trialkoxysilane having an amino or quaternary ammonium substituted alkyl group, are usually mixed before contacting the oil in water emulsion, so that a mixture of the tetraalkoxysilane and the trialkoxysilane is added to the emulsion. Alternatively the tetraalkoxysilane and the trialkoxysilane can be added separately but simultaneously to the oil in water emulsion, or can be added sequentially to the oil in water emulsion. If they are added sequentially, the tetraalkoxysilane is preferably added before the trialkoxysilane having an amino or quaternary ammonium substituted alkyl group.

The tetraalkoxysilane, and other water-reactive silicon compound if used, hydrolyses and condenses to form a network polymer, that is a 3-dimensional network of silicon-based material, around the emulsified droplets of the conditioning agent. A tetraalkoxysilane, for example, forms a 3-dimensional network consisting substantially of $SiO_{4/2}$ units. This network appears as a shell surrounding the droplets of conditioning agent.

The tetraalkoxysilane, and other water reactive silicon compound if used, can be added to the emulsion of conditioning agent as an undiluted liquid or as a solution in an organic solvent or in an emulsion form. The water reactive silicon compound and the emulsion are generally mixed under shear during addition and subsequently during condensation to form the silicon-based polymer shell on the surface of the emulsified droplets. Mixing can for example be by stirring, but it is preferred that the emulsion and the water reactive silicon compound are subjected to high shear, for example in a mixer of the rotor and stator type such as a Silverson (trade mark) mixer, either during addition of the water reactive silicon compound or after addition of the water reactive silicon compound and before formation of microcapsules is complete.

High shear mixing immediately after addition of the water reactive silicon compound is preferred. This leads to microcapsules of reduced particle size and appears to promote polymerisation of substantially all the tetraalkoxysilane and/or other water reactive silicon compound at the interface of the emulsion droplets.

The condensation reaction can be conducted at acidic, neutral or basic pH. The condensation reaction is generally carried out at ambient temperature and pressure, but can be carried out at increased temperature, for example up to 95° C., and increased or decreased pressure, for example under vacuum to strip the volatile alcohol produced during the condensation reaction. The weight ratio of conditioning agent to water reactive silicon compound is preferably at least 0.5:1 and in many cases may be at least 1.5:1, for example 2:1 to 9:1. Smaller microcapsules, for example those formed from a microemulsion, generally have a lower ratio of active material composition to water reactive silicon compound.

The particle size of the microcapsules produced generally corresponds to the particle size of the starting emulsion and can for example be in the range 0.1 to 200 µm, preferably lower than 30 µm, more preferably lower than 20 µm, more preferably lower than 16 µm, and preferably at least 0.5 µm, more preferably at least 1 µm. The emulsion particle size can for example be in the range 4 to 15 µm.

Microcapsules of particle diameter in the range 4 to 15 µm, for example 8 to 10 µm, may be particularly preferred. The diameter size of the microcapsules can be estimated with an optical microscope, for example by examining samples under a scanning electron microscope (SEM), or particle size measurements can be made by laser diffraction technique using a "Mastersizer 2000" from Malvern Instruments Ltd., UK, as described in the Examples below.

The shell thickness of the microcapsules depends on the weight ratio of conditioning agent to water reactive silicon compound and on the surface area of the emulsion droplets in the conditioning agent emulsion, which is inversely proportional to the droplet size for a given amount of conditioning agent. The shell thickness of the capsules is preferably in the range 2 to 50 nm, particularly between 5 and 20 nm, most preferably between 6 and 10 nm or between 10 and 15 nm. Microcapsules Shell Thicknesses are preferably determined by the physical relationships detailed in the examples It may be preferred to recover the microcapsules from suspension for dispersion in the liquid cleaning product. Recovery of the microcapsules can be achieved by any known liquid removal technique, for example by spray drying, spray chilling, filtering, oven drying or lyophilisation. Alternatively it may be preferred to add the suspension of microcapsules to the liquid cleaning product.

The encapsulated product can be post-treated with a water-reactive metal alkoxy or acyloxy compound. The metal compound should be gradually hydrolysed in water rather than immediately reacting with water; compounds of Group IVB, IVA or VA of the Periodic Table are suitable such as compounds of silicon, titanium, zirconium or vanadium. The water-reactive metal alkoxy or acyloxy compound can for example harden the shell of the microcapsules and/or make them more impermeable. The reactive metal alkoxy or acyloxy compound can for example be an alkoxysilane or acyloxysilane, particularly a trialkoxysilane such as methyl triethoxy silane or isobutyl triethoxy silane, or a silane having Si—H functionality such as tris (dimethylhydrogensilyloxy) n-octyl silane, or alternatively a titanium alkoxide (alkyl titanate).

The reactive metal alkoxy or acyloxy compound can have an organic functional group to promote adhesion to substrates, especially textile substrates, for example 3-methacryloxypropyl trimethoxy silane, 3-aminopropyl triethoxysilane, 3-aminopropyl trimethoxy silane, 3-glycidoxypropyl trimethoxy silane and 3-(2-aminoethylamino) propyl trimethoxy silane. The microcapsules can be post-treated with a reactive metal alkoxy or acyloxy compounds, e.g. an alkoxysilane to change their physical and/or chemical properties, for example by making the capsule surface more hydrophobic or more hydrophilic. For example, the microcapsule surface can be made more hydrophobic by reaction with a silane having a long chain alkyl group such as octyl triethoxy silane. As an alternative to chemical reaction the microcapsules can be coated with a material which alters their surface properties. The surface treatment can be carried out on the microcapsules in suspension or on the separated solid microcapsules.

A liquid laundry composition according to the invention generally comprises a surfactant and a fabric softening additive which is encapsulated as described above and in which the fabric or fibre conditioner is a fabric softener. The detersive surfactant usually forms from about 5% to 50% by weight of the liquid laundry composition. Detersive surfactants used can be of the anionic, nonionic, zwitterionic, ampholytic or cationic type or can comprise mixtures of these types. Most preferably the liquid laundry composition provides a wash solution pH from about 7 to about 9 and comprises at least one anionic and/or nonionic surfactant.

Because commercial laundry detergents are very much different some alterations in the capsules (generally shell thickness and/or particle size) may be required to ensure good dispersibility of the capsules in the detergent. Good dispersibility of the capsules is crucial for the good softening performance, Prior to making the washing tests one needs to make sure (for example by microscopy observation) that the capsules are well dispersed in the liquid detergent. It has been found that slight variation of the shell thickness can improve the dispersibility.

Preferred detersive anionic surfactants include the alkali metal and ammonium salts of organic sulphonates and sulphates having in their molecular structure an alkyl group of about 8 to about 20 carbon atoms. Examples of this group of synthetic surfactants are the sodium, potassium and ammonium alkyl sulfates, especially those obtained by sulfating the higher alcohols (8-18 carbon atoms), such as those produced by reducing the glycerides of tallow or coconut oil; b) the sodium, potassium and ammonium alkyl polyethoxylate sulfates, particularly those in which the alkyl group contains from 10 to 22, preferably from 12 to 18 carbon atoms, and wherein the polyethoxylate chain contains from 1 to 15, preferably 1 to 6 oxyethylene moieties; and c) the sodium and potassium alkylbenzene sulfonates in which the alkyl group contains from about 9 to about 15 carbon atoms, in straight chain or branched chain configuration, especially the linear alkylbenzene sulfonates in which the average number of carbon atoms in the alkyl group is from 11 to 13. Other useful anionic surfactants which can be used instead of or with the above synthetic surfactants in the liquid laundry composition are alkali metal soaps such as the sodium, potassium, ammonium, and alkylolammonium salts of higher fatty acids containing from about 8 to about 24, preferably 12 to 18 carbon atoms. Soaps can be made by direct saponification of fats and oils or by the neutralization of free fatty acids, for example the sodium and potassium salts of the mixtures of fatty acids derived from coconut oil or tallow.

Preferred detersive nonionic surfactants include ethoxylated fatty alcohols containing an alkyl group having 12 to 16 carbon atoms and 3 to 40 oxyethylene units, for example condensation products of C12-C15 alcohols with from about 5 to about 20 moles of ethylene oxide per mole of alcohol, ethoxylated alkylphenols containing an alkyl group having 8 to 12 carbon atoms and 3 to 40 oxyethylene units, and polyhydroxy fatty acid amides.

The liquid laundry composition may contain builders, for example 1 to 10% by weight of an alkali metal, ammonium or substituted ammonium polyacetate, carboxylate, polycarboxylate or polyhydroxysulfonate, an enzyme preparation containing protease, lipase and/or amylase enzymes, and a pH control agent or buffering agent. The liquid laundry composition is generally an aqueous composition containing for example 15 to 95% by weight water.

It may be preferred to add a dispersant to the liquid laundry composition to improve dispersion of the microcapsules in the composition, which is favourable to good performance of the composition. Examples of suitable dispersants are (block) copolymers containing poly-carboxylic acids as BASF's Glenium 250 cc, Glenium c327 and Glenium 21 or Silicone polyethers as for example that sold by Dow Corning under the Trade name DC 193. The dispersant helps prevent aggregation of the microcapsules and is particularly preferred when a transparent or translucent liquid laundry composition is desired. The dispersant can be added to the liquid laundry composition before addition of the microcapsules, but it is preferably added to the suspension of microcapsules if the encapsulated fabric softener is to be added to the laundry liquid as a suspension.

We have found that when fabrics are washed with a liquid laundry composition according to the invention containing an encapsulated fabric softening additive, improved softness of the fabrics is achieved compared to washing with the same liquid laundry composition containing the same amount of the same fabric softener which is not encapsulated, presumably due to improved retention of the softener on the fabric. We believe that encapsulation of the fabric softener protects it from solubilisation in the surfactant micelles of the wash, and that the fabric may act as a filter to retain the microcapsules, which subsequently break while rinsing and while spin drying to liberate the active fabric softener.

A hair shampoo composition according to the invention generally comprises a surfactant and a hair conditioner additive which is encapsulated as described above and in which the fabric or fibre conditioner is a hair conditioner. The hair cleaning surfactant usually forms from about 4% to 40% by weight of the shampoo. Hair cleaning surfactants used can be of the anionic, nonionic, zwitterionic, ampholytic or cationic type or can comprise mixtures of these types or more than one surfactant of the same type (ionic or nonionic). The shampoo composition preferably has a pH when wetted with water of around neutral, for example pH 4.5 to 9.5.

Examples of suitable anionic hair cleaning surfactants include sodium ethoxylated lauryl sulfate (sodium laureth sulfate or SLES), sodium lauryl sulphate, sodium alkylbenzenesulfonate, sodium xylenesulfonate, ammonium laureth sulfate, sodium polynaphthalenesulfonate, ammonium lauryl sulfate, and ammonium xylenesulfonate.

Examples of suitable cationic hair cleaning surfactants include quaternary ammonium halides such as octyl trimethyl ammonium chloride, dodecyl trimethyl ammonium chloride, hexadecyl trimethyl ammonium chloride, octyl dimethyl benzyl ammonium chloride, decyl dimethyl benzyl ammonium chloride, didodecyl dimethyl ammonium chloride, dioctadecyl dimethyl ammonium chloride, tallow trimethyl ammonium chloride and coco trimethyl ammonium chloride as well as corresponding hydroxides or other salts of these materials, fatty amines and basic pyridinium compounds, quaternary ammonium bases of benzimidazolines and polypropanolpolyethanol amines.

Examples of suitable amphoteric hair cleaning surfactants include cocamidopropyl betaine (CAPB), cocamidopropyl hydroxysulfate, cocobetaine, sodium cocoamidoacetate, cocodimethyl betaine, N-coco-3-aminobutyric acid and imidazolinium carboxyl compounds.

Examples of non-ionic hair cleaning surfactants include polyoxyalkylene alkyl ethers such as polyethylene glycol long chain (12-14 C) alkyl ether, polyoxyalkylene sorbitan ethers, polyoxyalkylene alkoxylate esters, polyoxyalkylene alkylphenol ethers, ethylene glycol propylene glycol copolymers, long chain fatty acid amides and their derivatives such as cocoamide diethanolamide (Cocoamide DEA), polyvinyl alcohol and alkylpolysaccharides.

Hair shampoo compositions according to the invention can contain other ingredients selected for example from perfumes, fragrances, colourants such as dyes, essential oils, vitamins, deposition agents such as polyquaternary compounds to improve the deposition of active ingredients from the shampoo onto hair, buffering agents, stabilizers and preservatives.

The conditioning agent may be encapsulated in a shell together with a perfume so as to provide an additive providing conditioning and perfuming benefits. The conditioning additive may also be used with a perfume additive containing a perfume or perfume precursor encapsulated in a shell, to get conditioning and perfuming additives.

Figure 1B:
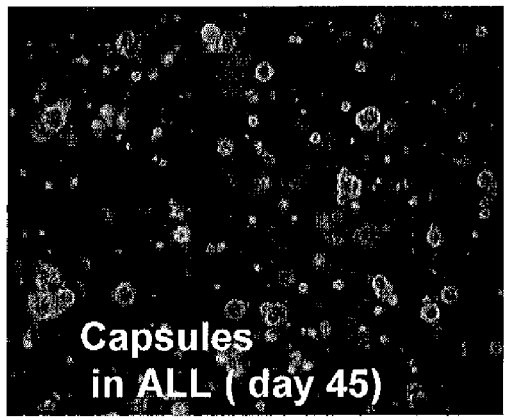
Figure 1B:
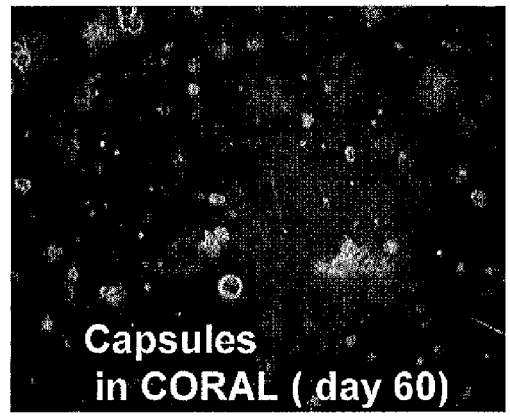
Figure 1B:
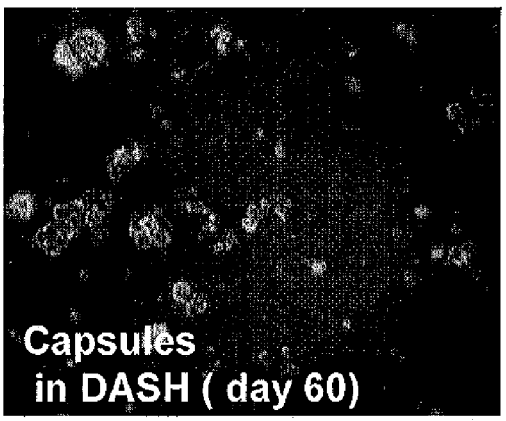
Figure 1B:
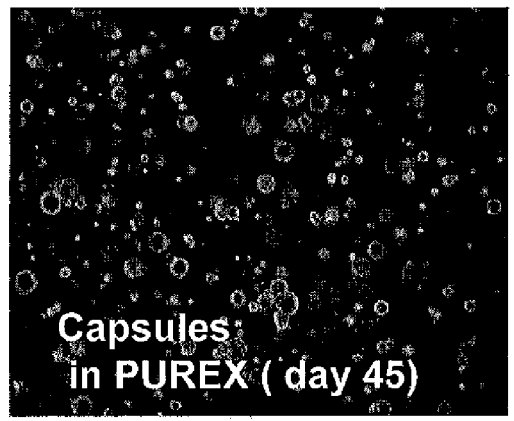

The invention is illustrated by the following Examples. The Examples will be described with reference to the accompanying drawings, of which FIG. 1A shows microphotographs of the concentrated dispersion of capsules produced in Preparation Example F1 and of dispersions of these capsules in two commercial liquid detergents, and of a dispersion of the emulsion of Preparation Example F3 in a commercial liquid detergent; and FIG. 1B shows microphotographs of dispersions of the capsules produced in Preparation Example F1 in four commercial liquid detergents after 45 or 60 days storage.

EXAMPLES PREPARATION

Example Preparation 1 (F1)

25 g amino siloxane polymer fabric softener was emulsified in 70 g water using 0.4 g solution of cetriamonium chloride (CTAC) at 29% and 0.5 g glacial acetic acid. Resulting emulsion was characterised as having D05 of 10 μm. 1.5 g TEOS was added and the polymerisation is allowed to proceed for 12 hours. At the end of the polymerisation 2.4 g dispersant was added and the capsules were agitated further 2 hours.

Example Preparation 2 (F2)

The same as F1, but instead of 1.5 g TEOS, 0.15 g of TEOS is added.

Example Preparation 3 (F3) Example of a Formulation NOT in the Scope of the Invention The same as F1 but instead of TEOS, 1.5 g water is added. This formulation is termed EMULSION in the examples below Example Preparation 4 (F4)

The same as F1, but instead of TEOS, 1.5 g mixture of (50:50) TEOS and a quaternary ammonium-substituted alkyl-trialkoxy silane 3-(trimethoxysilyl)-propyl-N,N-dimethyl-octadecylammonium chloride, (72 wt % in methanol), is added.

Example Preparation 5 (F5)

The same as F1, but instead of 1.5 g TEOS, 1.0 of TEOS is added.

Example Preparation 6 (F6)

The same as F1, but instead of 1.5 g TEOS, 0.5 g of TEOS is added.

Example Preparation 7 (F7)

The same as F1, but instead of 2.4 g dispersant 2.4 g water is added

Example Preparation 8 to 14 (E8- to F14)

These were prepared as EXAMPLE 4, but varying the ratio between TEOS and Alkyl-trialkoxy silane bearing a functionality comprising a quaternary nitrogen. These are shown in table 1

TABLE 1

| ingredients [g] | F4 | F8 | F9 | F10 | F11 | F12 | F13 | F14 |
|---|---|---|---|---|---|---|---|---|
| aminosiloxane | 25 | 25 | 25 | 25 | 25 | 25 | 25 | 25 |
| Water | 70 | 70 | 70 | 70 | 70 | 70 | 70 | 70 |
| CTAC (29%) | 0.4 | 0.4 | 0.4 | 0.4 | 0.4 | 0.4 | 0.4 | 0.4 |
| Acetic acid | 0.5 | 0.5 | 0.5 | 0.5 | 0.5 | 0.5 | 0.5 | 0.5 |
| TEOS | 0.75 | 1.485 | 1.425 | 1.35 | 1.2 | 0.6 | 0.375 | 0.3 |
| Quaternary alkoxysilane | 0.75 | 0.015 | 0.075 | 0.15 | 0.3 | 0.9 | 1.125 | 1.2 |
| Dispersant | 2.4 | 2.4 | 2.4 | 2.4 | 2.4 | 2.4 | 2.4 | 2.4 |

Example Preparation F15

34 g hydroxy-terminated polydimethyl siloxane having a degree of polymerisation (DP) of 866 was emulsified in 63.9 g water using 0.4 g solution of cetriamonium chloride at 29%, 0.2 g of polyoxyethylene (3) lauryl ether and 0.2 g 2.5M HCl. Resulting emulsion was characterised as having D05 of about 8 micrometre. A mixture of 1.3 g (50:50) TEOS and alkyltrialkoxy silane bearing a functionality comprising a quaternary nitrogen, 3-(trimethoxysilyl)-propyl-N,N-dimethyl-octadecylammonium chloride, (72 wt % in methanol, was added, and the polymerisation was allowed to proceed for 12 hours.

Example Preparation F16-F20

F16-F20 were prepared as F15 with ingredients described in table 2. Instead of silane the formulation F17 contained water. It is therefore a comparative example outside the scope of this invention.

TABLE 2

| ingredients [g] | F16 | F17 (Comparative) | F18 | F19 | F20 |
|---|---|---|---|---|---|
| polymer | 34 | 34 | 34 | 34 | 34 |
| DP (degree of polymerisation) | 1000 | 1000 | 866 | 1000 | 1000 |
| water | 63.9 | 65.2 | 63.9 | 63.9 | 63.9 |
| CTAC (29%) | 0.4 | 0.4 | 0.4 | 0.4 | 0.4 |
| 3-POE lauryl ether | 0.2 | 0.2 | 0.2 | 0.2 | 0.2 |
| HCl (2.5M) | 0.2 | 0.2 | 0.2 | 0.2 | 0.2 |
| TEOS | 0.65 | 0 | 0.65 | 1.04 | 1.04 |
| Quaternary alkoxysilane | 0.65 | 0 | 0.65 | 0.26 | 0.26 |
| D05 | 8 | 8 | 16 | 8.0 | 16 |

Microcapsules Shell thicknesses were determined by the following physical relationships:

$$\text{Shell Thickness (nm)} = ((D(v,0.5)/2) - (Dv0.5/2*(\text{Payload}/100)^{1/3}))*1000$$

With:

$D(v,0.5)$ expressed in microns.

Payload=Volume softening polymer*100/(Volume softening polymer+Volume shell).

Volume softening polymer=Weight softening polymer/Density softening polymer.

Volume shell=Weight shell/2.

The shell thicknesses of the microcapsules of Formulations F1 to F20 are shown in Table 3.

TABLE 3

| FORMULATION | SHELL THICKNESS |
|---|---|
| F1 | 10 |
| F2 | 1 |
| F3 | 0 |
| F4 | 18 |
| F5 | 8 |
| F6 | 4 |
| F7 | 12 |
| F8 | 12 |
| F9 | 12 |
| F10 | 13 |
| F11 | 14 |
| F12 | 19 |
| F13 | 21 |
| F14 | 22 |
| F15 | 12 |
| F16 | 12 |
| F17 | 0 |
| F18 | 23 |
| F19 | 9 |
| F20 | 18 |

Particle size measurements here specified were made by laser diffraction technique using a "Mastersizer 2000" from Malvern Instruments Ltd., UK, and further information on the above particle sizes can e.g. be found in "Basic principles of particle size analytics", Dr. Alan Rawle, Malvern Instruments Limited, WR14 1XZ, UK and the "Manual of Malvern particle size analyser". Particular reference is made to the user manual number MNA 0096, Issue 1.0, November 1994. All particle sizes indicated in the present application were mean average particle size according to D(v, 0.5) and were measured with a Malvern Mastersizer; scattering pattern being analysed in the lines of the Mie theory, if nothing else is stated or obvious.

Example 1

Stability of the Dispersion Versus an Emulsion

This example proved the utility of the invention for the compatibilization of a softening agent in a fully formulated commercial HDL under the form of micron-sized particles. To various commercial liquid detergents we added either a silicone emulsion (formulation F3) or capsules containing the same silicone polymer (Formulations F1 or F2) as in the emulsion, at the same mass ratio polymer/detergent.

Samples of thus obtained 2-in-1 liquid detergents were observed in transmitted illumination using a Zeiss microscope equipped with long focus 20× objective (in this case AXIOPLAN from Zeiss) a sensitive live-image CCD camera (25 frames/second) connected to the frame grabber. HDL/

Emulsion and HDL/Capsules mixtures were loaded between standard microscope lamella and observed at regular time intervals.

15 to 20 minutes after the mixing the silicone emulsion incorporation no emulsion droplets could be observed whereas when using the encapsulated silicone polymer dispersion capsules were observed even after month's hours of storage.

FIG. 1A shows typical micrographs of mixtures liquid-detergent emulsion and liquid detergent-capsules taken 15-20 minutes after the mixing. FIG. 1B showed that dispersion was stable in various liquid detergents for many weeks.

FIG. 1a Text Description

When observed in transmitted illumination (light microscopy) the dispersions in this case preparation F1 reveal spherical objects of core shell structure.

The same dispersions were mixed with a liquid detergent (for example Regular Tide (Trade Mark) or OMO (Trade Mark)) at 3% of silicone active. As a comparison, the emulsion prior to encapsulation (formulation F3) was mixed with the same two commercial detergents.

Non-encapsulated emulsion droplets were unstable in detergent and 15-20 minutes after the mixing these droplets are no longer visible in microscopy. Without being bond to any theory, it was believed that this "disappearance" was due to the molecular solubilisation of the silicone active in the matrix of the detergent. On the contrary, the encapsulated emulsion (F1, capsule thickness of 10 nm) was stable in the detergent and no visual change was observed.

FIG. 1b Text Description

The capsules of F1 were dispersed at 3% silicone active in various commercially available detergents. These preparations were observed in light microscopy in transmitted illumination. After 45 or 60 days of storage the capsules are still intact and the observation reveals the same structure as at the day one.

Each of samples F15-F20 was mixed with a commercial detergent at a ratio of 1% silicone active in the final blend. The obtained blends were observed using a microscope as described. Very good dispersibility of the capsules was observed. The blends were then placed in a climatic chamber for 4 weeks at 40° C. At the end of the ageing process the blends were again observed using a microscope. No capsules were detected in sample F17 (out of the scope of the invention). The appearance of the F15, F16 and F18 to F20 was similar to what was observed before ageing. Some traces of bulk silicone were detected on the walls of the containers of F18 and F20. Microcapsules of F15, F16 and F19 which have D05 below 15 μm are more stable than larger microcapsules of F18. and F20.

Example 2

Influence of the Shell Thickness

Example 1 showed that the shell protects the polymer from being completely dissolved in the HDL. This example 2 demonstrated the importance of the polymeric shell for the protection of the encapsulated active. To quantify the dissolution of the active in the matrix of the detergent we have used turbidity measurements performed on Turbiscan M 2000 instrument. Since liquid detergents are frequently transparent or translucent, the presence of microscopic particles should reduce the transmittance of the detergent, increasing the turbidity. Similarly, the disappearance of emulsion droplets/particles leads to a decrease in the turbidity and increase of the transmittance.

Table 4 shows the transmittance of various 2-in-1 formulations recorded in the course of several weeks. Each sample was measured at two different heights from the bottom of the vessel containing the HDL/capsules mixture (A-4 cm from the bottom, B-5 cm from the bottom). Prior to each measurement each sample was homogenized to re-disperse the creamed species. Table 4 shows that the destabilization in case of F6 was considerable already 4 days after the preparation, while capsules of thicker shells exhibited a very good stability along time.

TABLE 4

| TIME/ min | Transmittance F1 in Regular TIDE at 3% Si active | | TIME/ min | Transmittance F5 in Regular TIDE at 3% Si active | | TIME/ min | Transmittance F6 in Regular TIDE at 3% Si active | |
|---|---|---|---|---|---|---|---|---|
| | A | B | | A | B | | A | B |
| 0 | 0.01807 | 0.01807 | 0 | 0.03183 | 0.03117 | 0 | 0.04893 | 0.04305 |
| 44 | 0.02324 | 0.02029 | 1 | 0.03296 | 0.03247 | 30 | 0.07681 | 0.07173 |
| 45 | 0.02292 | 0.02063 | 33 | 0.03764 | 0.03764 | 82 | 0.07956 | 0.07433 |
| 178 | 0.02773 | 0.02493 | 173 | 0.04265 | 0.04166 | 107 | 0.08531 | 0.07729 |
| 10308 | 0.02892 | 0.02727 | 10305 | 0.0587 | 0.05608 | 1510 | 0.10986 | 0.10936 |
| 39078 | 0.05125 | 0.04831 | 46277 | 0.08533 | 0.08253 | 6111 | 0.27901 | 0.2541 |
| 46276 | 0.04602 | 0.03651 | 46278 | 0.08772 | 0.08347 | 10311 | 0.36179 | 0.37131 |
| 46277 | 0.04326 | 0.03915 | 72191 | 0.1091 | 0.1091 | 39066 | 0.43842 | 0.41559 |
| 72000 | 0.0553 | 0.0553 | | | | 46322 | 0.55167 | 0.53458 |
| | | | | | | 72183 | 0.75615 | 0.82 |

As reference, Regular Tide was observed. At time 0, the transmittance at A and B were 0.9289. At time 80000, A was 0.92 and B was 0.9269.

Example 3

Presence of the Dispersing Agent (Dispersant)

Encapsulated fabric softener with (F1) and without dispersant (F7) was added to a commercial detergent at a ratio of 3% aminosiloxane active. In all cases the size of the capsules was 11 um, (D(v,0.5) measured as described previously).

Visual assessment with direct eye observation was made by the operator. Bottle A with detergent+F7 was compared to bottle B containing detergent+F1. A big lump apparent similar to an egg white was observed in bottle A, which could not be re-dispersible. No lump was apparent in bottle B; the liquid appeared to be homogenous. It is believed that the presence of a which is a polymer which is most probably adsorbed on the shell of the capsule, thus preventing the osmotic shock caused by the high surfactant concentration in the liquid detergent.

Example 4

Softening Benefits

Panel Test on Softness Benefit

This test was performed to determine the softness of dry fabrics (towels in particular) after wash cycle.

Fabrics pre-conditioning.

This step was performed to remove silicone (or any other) treatment made during manufacturing of fabrics and to be sure that loads are free of silicone/surface treatment agents before the specific treatment of this invention.

Load was made with 5 new pillow cases and 4 little terry towels (30×50 cm) and was of 1.0 kg.

This load was washed 4 times in the following conditions:

Prewash 1: Miele W934—long program—water hardness: 0° F.-20 g Dash powder—Temperature: 95° C.—Spin rate: 600 rpm Blank 1: Miele W934—long program—water hardness: 0° F.—No detergent—Temperature: 95° C.—Spin rate: 600 rpm Prewash 2: same conditions that in prewash 1

Blank 2: same conditions that blank 1

The complete cycle of pre-conditioning was always made in the same type of washing machine (Miele W377, W934 or W715). In order to save some time, 3 loads could be prewashed at the same time in the same washing machine. The total load is then 3.0 kg and the quantity of detergent powder was then adjusted to 60 g.

Homemade HDL.

Homemade HDL was mixture of 15.70% Maranil paste A5 (trade name), 7.30% Dehydrol LT7 (trade name), 3.23% silicone antifoam, 8.06% soda ash and 66.53% water.

Fabric treatment.

2 or 3 treatments were made in parallel on 2 or 3 different washing machines at the same time. There was always one reference treatment washed with a commercial liquid detergent containing fabric softener and 1 or 2 treatments with product to be tested. All fabrics from different treatments were line-dried at the same time at room temperature (temperature and relative humidity must be controlled or the same for a set of comparison).

Panel test.

Generally each panellist was presented two, three or four towels. One, two or three towels respectively were treated with experimental formulation, and one was a reference, i.e. washed with a commercial liquid detergent containing fabric softener. One terry towel was used for 4 panellists and after was replaced by another one. Following questions were asked to 16 or 20 panellists.

"Which towel is the softer?"

"If the first fabric is the reference and quoted 5 on a scale of 1 to 10 how would you rate (the) other(s), considering 10 means very soft, smooth?"

Table 5 shows the results obtained with a panel of 16 testers. 'Reference' is commercial liquid detergent sold under the Trade Mark 'Dash 2-in-1'.

TABLE 5

|  | Detergent | Additive | Example Formulation added | Average Score |
|---|---|---|---|---|
| test 1 | Reference | NO | No | 5 |
|  | Persil Naturals | NO | F1, 3% Si active | 4.3 |
|  | Persil Naturals | 0.1% cond. Polymer | F1, 3% Si active | 5.5 |
| test 2 | Reference | NO | No | 5 |
|  | Homemade HDL | NO | F1, 3% Si active | 5.2 |
|  | Homemade HDL | 0.1% cond. Polymer | F1, 3% Si active | 6.7 |
| test 3 | Reference | NO | No | 5 |
|  | Dash regular | No | No | 4.6 |
|  | Dash regular | No | F1, 3% Si active | 5. |
| test 4 | Reference | NO | No | 5 |
|  | Dash regular | No | F1, 3% Si active | 6. |
|  | Dash regular | No | F3, 3% Si active | 5.0 |

Test 1 showed that doping a commercial detergent with an encapsulated fabric softener according to the invention and a conditioning agent gave better results than the commercial reference Test 2. Illustrated that the material made a homemade detergent better than a commercial reference and even better when a conditioning polymer was used Test 3 illustrated the same thing as test 1, but on a different commercial detergent.

Test 4 Illustrates that adding the emulsion without the shell (F3) does not work, i.e. we need the encapsulation

Example 5

Composition of the Shell

Capsules prepared following formulations F4, F8, F10, F11 were mixed with a commercial detergent at 3% active level. Thus obtained doped detergents were used in panel testing following the protocol provided in the previous example. Table 6 summaries the results. Towels treated by F4 and F11 were described as "substantially softer" than the towels washed by the detergent alone. Samples F8 and F10 did also provide towels softer than the ones washed with detergent alone, but slightly less softer than the chosen reference.

TABLE 6

|  | Detergent | Additive | Formulation example added | Average Score |
|---|---|---|---|---|
| Test 5 | Reference | No | NO | 5 |
|  | Commercial Detergent | NO | Nothing added | 3.5 |
|  | Commercial Detergent | NO | F8, 3% Si Active | 3.9 |
|  | Commercial Detergent | NO | F11, 3% Si active | 4.6 |
|  | Commercial Detergent | NO | F4, 3% Si Active | 4.8 |
|  | Commercial Detergent | NO | F10, 3% Si Active | 4.3 |

Example 6

Alternative Polymer

Each sample F15-F20 was compared one by one to original commercial detergent, applying a forced ranked panel assessment as explained above, but a panel of 20 was selected. These tests were preformed both on the fresh and on the aged blends. The panelist were presented two towels and a score of 5 was assigned to the towels washed with the original (reference) detergent. The average score for each detergent-capsules blend was obtained as the arithmetic mean of the score given by 20 panellists. The results are listed in Table 7.

All formulations F15-F20 gave better results than reference when the mixture formulation-HDL were fresh. However after aging in the detergent-formulation mix, the mix containing F17 formulation became unstable and an oily droplet was visible on the detergent surface after ageing. Therefore the panel test was not run for this aged blend. Towels treated with the aged detergent comprising formulations according to the invention were positively perceived by the panellists.

TABLE 7

|  | Detergent | Additive | Formulation example added | Average Score fresh | Average score aged 4 w/40 C |
|---|---|---|---|---|---|
| Test 6 | Commercial Detergent | NO | Nothing added (reference) | 5.0 |  |
|  | Commercial Detergent | NO | F15, 1% Si active | 5.9 | 5.2 |
|  | Commercial Detergent | NO | F16, 1% Si active | 5.8 | 5.1 |
|  | Commercial Detergent | NO | F17, 1% Si active | 5.8 | Unstable |
|  | Commercial Detergent | NO | F18, 1% Si active | 5.7 | Not tested |
|  | Commercial Detergent | NO | F19, 1% Si active | 5.9 | 6.1 |
|  | Commercial Detergent | NO | F20, 1% Si active | 5.8 | Not tested |

The invention claimed is:

1. A fabric, fibre, hair or skin conditioning additive for use in a liquid cleaning product, wherein a fabric, skin, hair or fibre conditioning agent is encapsulated within a shell comprising a silicon-containing polymer network, and wherein the silicon-containing polymer network is a polymerization product of a reaction between a tetraalkoxysilane and an alkoxysilane having an amino or quaternary ammonium substituted alkyl group.

2. The conditioning additive according to claim 1, wherein the alkoxysilane having an amino or quaternary ammonium substituted alkyl group has the formula $R'_3$13 Si—Y—N+$R''_3$, wherein each group R' is an alkoxy group having one or two carbon atoms, each group R'' is an alkyl group having 1 to 18 carbon atoms, and Y is a divalent organic radical of the formula $C_nH_{2n}$ where n is an integer from 1 to 18.

3. The conditioning additive according to claim 1, wherein the conditioning agent comprises a polyorganosiloxane.

4. The conditioning additive according to claim 3, wherein the conditioning agent comprises an amino-functional polyorganosiloxane.

5. The conditioning additive according to claim 4, wherein the amino-functional polyorganosiloxane has the formula:

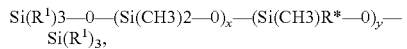
$Si(R^1)_3$—O—$(Si(CH3)2$—O$)_x$—$(Si(CH3)R*$—O$)_y$—$Si(R^1)_3$, where R* is an aminoalkyl group having 1 to 30 carbon atoms and 1 to 5 nitrogen atoms, each group $R^1$ is selected from alkoxy groups having 1 to 4 carbon atoms, hydrocarbon groups having 1 to 18 carbon atoms and or aminoalkyl groups having 1 to 18 carbon atoms and 1 to 3 nitrogen atoms, and x and y are integers between 1 and 100, y being less than 0.1x.

6. The conditioning additive according to claim 1, wherein the conditioning agent comprises a polydimethyl siloxane which is trimethyl- or hydroxy-terminated.

7. The conditioning additive according to claim 6, wherein the polydimethyl siloxane has a DP in the range of 100 to 5000.

8. The conditioning additive according to claim 1, wherein the mean volume diameter of the capsules, including the shell, is within the range 2 to 30 μm.

9. The conditioning additive according to claim 1, wherein the shell thickness of the capsules is between 5 and 20 nm.

10. A process for preparing an encapsulated fibre, skin, hair or fabric conditioning additive, the process comprising adding a liquid composition comprising a water reactive silicon compound (composition A) to an aqueous emulsion of a fibre, skin, hair or fabric conditioning agent (composition B), thereby condensing and polymerising the composition A at its interface with the emulsified droplets of the composition B to form microcapsules, wherein the composition B has a core of the fibre, skin, hair or fabric conditioning additive surrounded by a shell comprising a silicon-based polymerized network, wherein the silicon-based polymerized network is a polymerization product of a reaction between a tetraalkoxysilane and an alkoxysilane having an amino or quaternary ammonium substituted alkyl group and wherein the composition B comprises a cationic aqueous emulsion containing 10 to 50% by weight of an amino-functional polyorganosiloxane.

11. A process according to claim 10, wherein the liquid composition A comprises a liquid tetraalkoxysilane.

12. A liquid laundry detergent composition comprising a surfactant and a fabric conditioning additive according to claim 1.

13. A liquid hair cleaning composition comprising a surfactant and a hair conditioning additive according to claim 1.

14. A liquid personal care composition comprising a surfactant and a skin conditioning additive according to claim 1.

15. An encapsulated polyorganosiloxane in a liquid laundry detergent composition, wherein the encapsulated polyorganosiloxane is encapsulated within a shell, wherein the shell comprises a silicon-containing polymer network, and wherein the silicon-containing polymer network comprises a polymerization product of a reaction between a tetraalkoxysilane and an alkoxysilane having an amino or quaternary ammonium substituted alkyl group.

16. A process for preparing an encapsulated fibre, skin, hair or fabric conditioning additive, the process comprising adding a liquid composition comprising a water reactive silicon compound (composition A) to an aqueous emulsion of a fibre, skin, hair or fabric conditioning agent (composition B), thereby condensing and polymerising the composition A at its interface with the emulsified droplets of the composition B to form microcapsules, wherein the composition B has a core of the fibre, skin, hair or fabric conditioning agent surrounded by a shell comprising a silicon-based polymerized network, and wherein the silicon-based polymerized network is a polymerization product of a reaction between a tetraalkoxysilane and an alkoxysilane having an amino or quaternary ammonium substituted alkyl group.

17. The conditioning additive according to claim 2, wherein the conditioning agent comprises a polyorganosiloxane.

* * * * *